(12) United States Patent
Ducharme et al.

(10) Patent No.: US 10,987,101 B2
(45) Date of Patent: Apr. 27, 2021

(54) SUPERELASTIC BONE COMPRESSION STAPLE

(71) Applicant: ORTHO SOLUTIONS HOLDINGS LIMITED, Littleton, CO (US)

(72) Inventors: Dustin Ducharme, Littleton, CO (US); Alister Maclure, Chelmsford (GB); Kevin Stamp, Sheffield (GB)

(73) Assignee: ORTHO SOLUTIONS HOLDINGS LIMITED, Littleton, CO (US)

( * ) Notice: Subject to any disclaimer, the term of this patent is extended or adjusted under 35 U.S.C. 154(b) by 0 days.

(21) Appl. No.: 16/227,675

(22) Filed: Dec. 20, 2018

(65) Prior Publication Data
US 2019/0192140 A1    Jun. 27, 2019

Related U.S. Application Data

(60) Provisional application No. 62/609,591, filed on Dec. 22, 2017.

(51) Int. Cl.
*A61B 17/064* (2006.01)
*A61B 17/068* (2006.01)
*A61B 17/10* (2006.01)
*A61B 17/00* (2006.01)

(52) U.S. Cl.
CPC ...... *A61B 17/0642* (2013.01); *A61B 17/0644* (2013.01); *A61B 17/0682* (2013.01); *A61B 17/10* (2013.01); *A61B 2017/00867* (2013.01); *A61B 2017/0641* (2013.01); *A61B 2017/0645* (2013.01)

(58) Field of Classification Search
CPC ........ A61B 2017/00867; A61B 17/064; A61B 2017/0641; A61B 17/0642; A61B 17/0644; A61B 2017/0645; A61B 17/0682; A61B 17/10; A61B 17/809
See application file for complete search history.

(56) References Cited

U.S. PATENT DOCUMENTS

| | | | |
|---|---|---|---|
| 3,741,205 A * | 6/1973 | Markolf | A61B 17/7059 606/291 |
| 5,350,400 A * | 9/1994 | Esposito | A61B 17/0644 606/219 |
| 5,695,524 A | 12/1997 | Kelley et al. | |
| 5,715,987 A | 2/1998 | Kelley et al. | |
| 6,059,787 A | 5/2000 | Allen | |
| 6,083,242 A | 7/2000 | Cook | |
| 6,325,805 B1 * | 12/2001 | Ogilvie | A61B 17/70 606/75 |

(Continued)

FOREIGN PATENT DOCUMENTS

| | | |
|---|---|---|
| AU | 2013206096 B2 | 1/2014 |
| CA | 2817333 A1 | 12/2013 |

(Continued)

*Primary Examiner* — Larry E Waggle, Jr.
(74) *Attorney, Agent, or Firm* — Hudak, Shunk & Farine Co. LPA

(57) ABSTRACT

The invention is a staple comprising a bridge member having a spherical top surface and a spherical opposing bottom surface defining a constant thickness between and having a constant thickness and a first pair of a first leg and a second leg and a second pair of a first leg and a second leg where the first and second pair of legs are spaced apart along the axis and are joined to the bridge member.

12 Claims, 5 Drawing Sheets

DETAIL E
SCALE 25:1

(56) References Cited

U.S. PATENT DOCUMENTS

| | | | |
|---|---|---|---|
| 6,336,928 B1* | 1/2002 | Guerin | A61B 17/7059 606/282 |
| 6,348,054 B1 | 2/2002 | Allen | |
| 6,783,531 B2 | 8/2004 | Allen | |
| 7,556,647 B2* | 7/2009 | Drews | A61B 17/064 623/2.11 |
| 7,867,265 B2* | 1/2011 | Beutter | A61B 17/0642 606/324 |
| 8,021,389 B2* | 9/2011 | Molz, IV | A61B 17/0642 206/339 |
| 8,235,995 B2 | 8/2012 | Focht et al. | |
| 8,584,853 B2 | 11/2013 | Knight et al. | |
| 8,596,514 B2 | 12/2013 | Miller et al. | |
| 8,721,646 B2 | 5/2014 | Fox | |
| 8,808,294 B2* | 8/2014 | Fox | A61B 17/68 606/75 |
| 9,017,331 B2 | 4/2015 | Fox | |
| 9,095,338 B2 | 8/2015 | Taylor et al. | |
| 9,101,349 B2 | 8/2015 | Knight et al. | |
| 9,204,932 B2 | 12/2015 | Knight et al. | |
| D748,258 S | 1/2016 | Gledel | |
| 2002/0173793 A1 | 11/2002 | Allen | |
| 2010/0063506 A1 | 3/2010 | Fox et al. | |
| 2012/0228355 A1 | 9/2012 | Combrowski et al. | |
| 2013/0026206 A1 | 1/2013 | Fox | |
| 2013/0041406 A1 | 2/2013 | Bear et al. | |
| 2013/0206815 A1 | 8/2013 | Fox | |
| 2013/0231667 A1* | 9/2013 | Taylor | A61B 17/0642 606/75 |
| 2013/0331839 A1 | 12/2013 | Hester et al. | |
| 2014/0014553 A1 | 1/2014 | Knight et al. | |
| 2014/0018809 A1 | 1/2014 | Allen | |
| 2014/0020333 A1 | 1/2014 | Knight et al. | |
| 2014/0034702 A1 | 2/2014 | Miller et al. | |
| 2014/0097228 A1 | 4/2014 | Taylor et al. | |
| 2014/0277516 A1 | 9/2014 | Miller et al. | |
| 2016/0235460 A1 | 8/2016 | Wahl | |
| 2017/0065275 A1* | 3/2017 | Cheney | A61B 17/0642 |
| 2017/0100163 A1 | 4/2017 | Palmer et al. | |
| 2017/0231625 A1 | 8/2017 | Handie | |
| 2017/0281157 A1 | 10/2017 | Hartdegen et al. | |
| 2018/0289366 A1 | 10/2018 | Morgan et al. | |
| 2018/0353172 A1 | 12/2018 | Hartdegen et al. | |
| 2019/0046182 A1 | 2/2019 | Krumme | |
| 2019/0231349 A1 | 8/2019 | Wahl et al. | |
| 2019/0282231 A1 | 9/2019 | Vasta | |
| 2020/0000464 A1 | 1/2020 | Gaston et al. | |
| 2020/0008807 A1 | 1/2020 | Hollis | |
| 2020/0038076 A1 | 2/2020 | Amis et al. | |
| 2020/0100820 A1 | 4/2020 | Hollis et al. | |

FOREIGN PATENT DOCUMENTS

| | | | |
|---|---|---|---|
| CN | 103479409 A | 1/2014 | |
| CN | 102579116 B | 12/2015 | |
| CN | 103732155 B | 9/2017 | |
| DE | 102012100086 A1 | 8/2012 | |
| EP | 1179994 B1 | 6/2006 | |
| EP | 1772107 A1 | 11/2007 | |
| EP | 2474271 A2 | 11/2012 | |
| EP | 2736421 B1 | 6/2014 | |
| EP | 2671517 B1 | 3/2017 | |
| EP | 2741683 B1 | 7/2019 | |
| JP | 2013255796 A | 12/2013 | |
| WO | WO-2009091770 A1 * | 7/2009 | A61B 17/0642 |
| WO | 2013055824 A1 | 4/2013 | |
| WO | 2013130978 A2 | 9/2013 | |
| WO | 2014058954 A2 | 4/2014 | |
| WO | 2014120955 A1 | 8/2014 | |

* cited by examiner

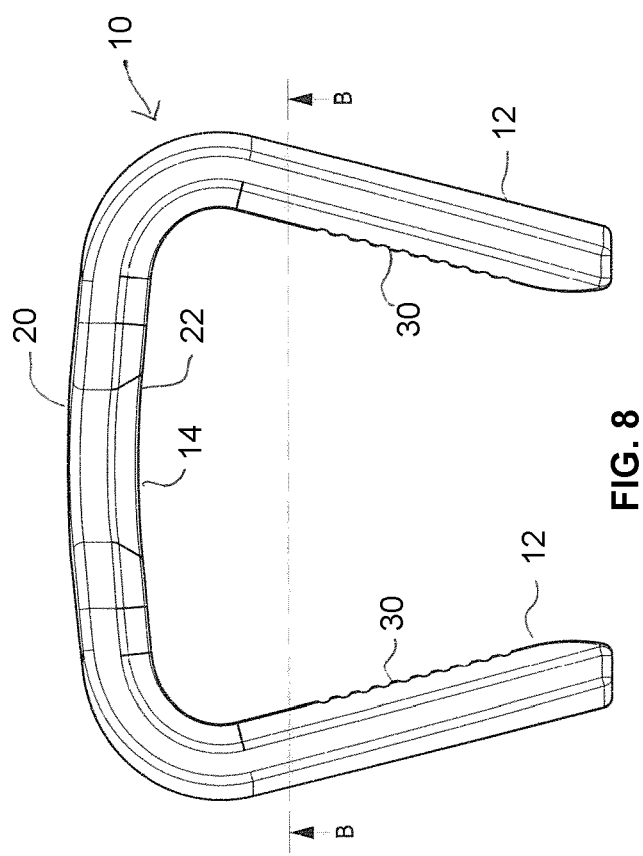
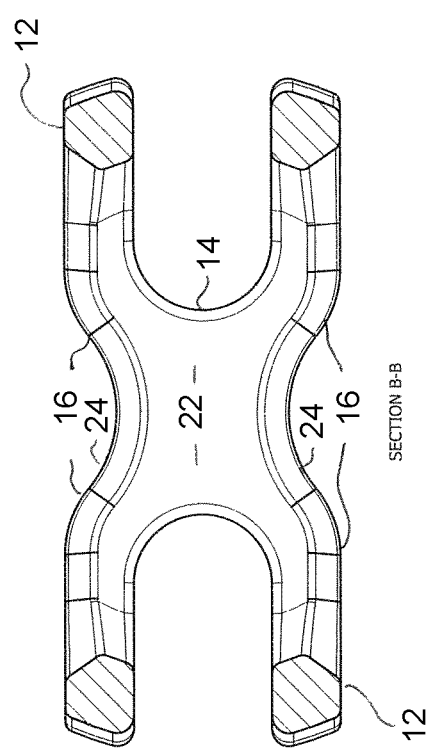

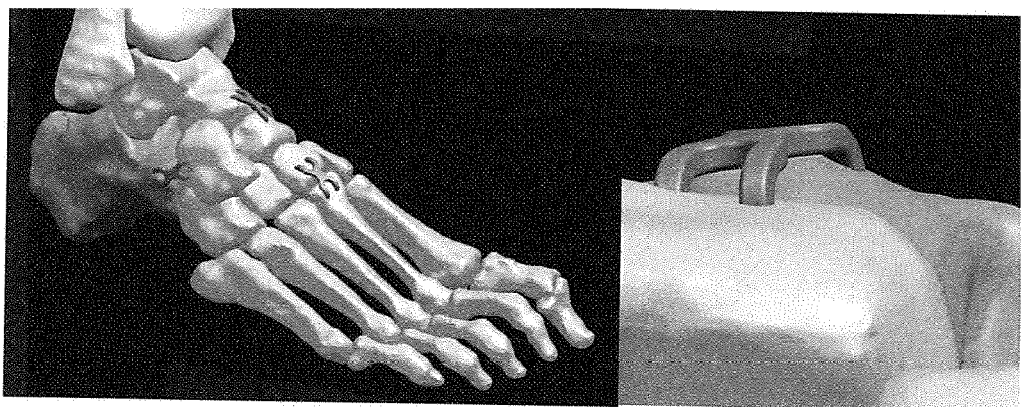
FIG. 11(a)          FIG. 11(b)

SUPERELASTIC BONE COMPRESSION STAPLE

FIELD OF THE INVENTION

The present invention relates to a room temperature superelastic bone compression staple intended for bone fixation in the surgical management of fractures and reconstruction of the foot and hand. The staple is fabricated by machining a blank to form a staple in the closed (converging legs) shape and the resulting staple is mechanically deformed during use to induce the superelastic shape memory properties to compress bone segments and facilitate osteosynthesis. The staple has a bridge member preferably having a uniform thickness defined between an exterior and corresponding opposing interior surface each configured as a portion of a sphere. The bridge member joins two to four legs also having a unique configuration, such as a polygonal cross-section, and optional texturing or barbs on one or more surfaces to increase the anchoring of the legs in bone. The staple is provided having a range of different bridge widths ranging from 10 mm to 25 mm and various leg lengths in the same range of length, so as to accommodate different fixation procedures in the forefoot, midfoot, rearfoot and hand. Optimally, the staple is supplied pre-assembled on an inserter or introducer in a sterile procedure pack containing disposable instrumentation.

BACKGROUND OF THE INVENTION

Initial bone staples were temperature activated memory staples, which were rendered obsolete through the adoption of mechanically activated room temperature superelastic Nitinol devices as the relevant materials technology advanced to the current state of the art.

Over 1.8 million orthopaedic trauma fixation procedures were performed in the US in 2016, which is expected to remain the fastest growing segment through to 2025 and is expected to reach over $4 billion by 2025, and the fastest growing part of this market is the staple fixation segment. The primary driver for growth is reportedly a reduced operating time as compared to screws, and plates.

While this growth demonstrates that orthopedic arts have accepted bone staples as an alternative and even a preferred fixation hardware to screws and bone plates for certain procedures, there remain issues and limitations to the designs presently available. While the latest generation of memory staples have improved rigidity and compressive capability when used alone or as adjunctive hardware, (which could improve outcomes for certain procedures, such as the Lapidus arthrodesis), it is still desirable to provide a stiffer and stronger construct and more reproducible surgical technique than the generally accepted perpendicular arrangement of legs and bridge used for example for a first metatarsophalangeal arthrodesis procedure. Additionally, the prior art devices are not optimal for fracture and osteotomy fixation of the hand and foot, including joint arthrodesis and to stabilize and dynamically compress bone fragments to facilitate osteosynthesis.

In response to these and other concerns, the present staple has a low-profile design to respect the economy of space in small bone procedures and further is designed for quick and efficient use, including removal following bone fusion. Additional issues with the prior art staples include problems with packaging, implant or instrument breakage, incompatibility with the staple inserter or other related instruments, lack of compression or sustained compression within the bone/implant construct, and difficulties with the instrument and implantation process.

A known risk with the prior art staples is associated with over-spreading the staple, which can over-stress the staple legs and have a deleterious effect on mechanical properties, recoverable strain and fatigue resistance. The present invention reduces this risk through design improvements achieved in manufacture of the staple and in the configuration of the legs and a resultant reinforcement of the leg/bridge interface.

The present staple has a unique configuration that addresses the issues of breakage while providing a low profile implant that is particularly well suited for small bone procedures. The staple and staple inserter are designed to function together to avoid over-spreading and/or misalignment of the staple legs so as to reduce potential use risks and to provide a device which is inherently less prone to user error. In addition, the staple is designed for permanent implantation or unlike prior art devices, for removal following bone fusion which can typically take 4-6 weeks while the patient is partially weight bearing. Specific instrumentation is provided for the removal procedure.

The staple will be manufactured from ASTM F2063 room temperature superelastic (e.g., from 2 to up to 8%) Nitinol. (and it will be understood that other shape memory materials can be used in this design).

SUMMARY OF THE INVENTION

The present invention relates to a superelastic Nitinol staple having one or two pairs of spaced legs joined by a bridge member is "straight-backed" meaning that it extends along an axis to form a "table-top" type of configuration more notable in the energized state in which the legs are substantially transverse to the bridge member, however, with a rounded top surface. In fact, the top surface is advantageously curved in two dimensions, i.e., along the axis and transverse to it to provide a segment of a sphere or torroid. This provides a staple having a low profile straight-backed configuration which suits implantation in the small bone environment, in particular for use in osteotomies, fusions or other osteo synthesis procedures.

In addition, the staple has two, three, or four legs on either end of the bridge member. The legs may be joined to the bridge member by corner extensions which flow into the legs or may extend directly from the bridge for example from an inwardly curved recess in the ends of the bridge member. The legs preferably have a uniform cross-sectional shape which helps to eliminate stress risers, for example, at the conjunction of the legs and bridge. One optimal shape is a FIVE-sided polygon, such as pentagon. The staple is designed for optional removal, so that while the staple may include texturing, ridges, or barbs to improve the hold in bone, the amount of mechanical interference is limited, for example by the provision of low ridges and on one only one or two surfaces of the legs, such as on the inner surface facing inward on the leg. Thus, the staple design permits easy removal.

BRIEF DESCRIPTION OF THE DRAWINGS

FIG. 8 shows a side view of the staple of FIG. 1 showing where the section of FIG. 9 is taken;

FIG. 9 shows a cross section of the staple of FIG. 8;

FIGS. 11(a) and 11(b) shows a view of the staple of FIG. 1 in position on a human mid-foot;

DETAILED DESCRIPTION OF THE INVENTION

Figure 3:
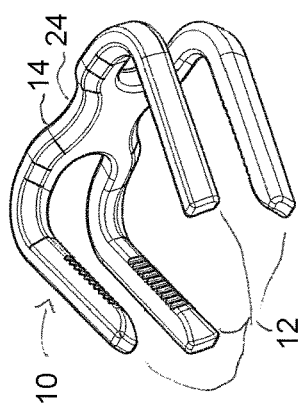
FIG. 3 shows a bottom perspective view of the staple of FIG. 1.
Figure 6:
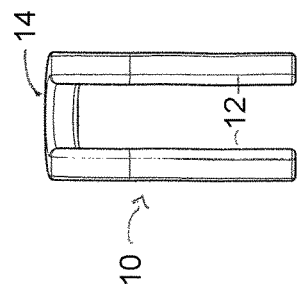
FIG. 6 shows a second end view of the staple of FIG. 1.
Figure 2:
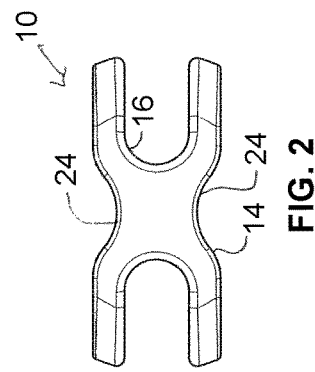
FIG. 2 shows a top view of the staple of FIG. 1.
Figure 5:
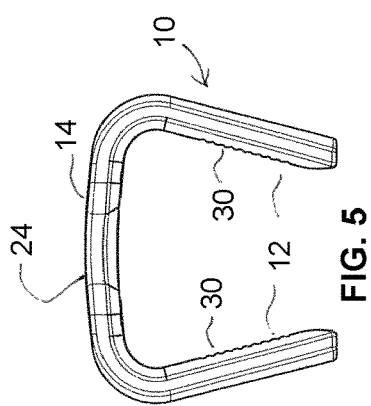
FIG. 5 shows a side view of the staple of FIG. 1.

The present invention relates to a room temperature superelastic Nitinol bone compression staple 10. The staple 10 has two or more, and preferably 2, 3, or 4 legs 12 that will engage bones or bone segments through the cortical surfaces. The legs 12 are spaced apart from each other and joined together by bridge member 14 that extends across the area between legs at either end of the bridge member 14. As shown, the legs are joined to transitional extensions 16 which fold or curve at an angle of from 75° to 90°, and preferably from 85° to 90° relative to a long axis of the bridge member. On the other end, the extensions 16 join to the bridge member 14 and the bridge member has an inwardly curved recess between the legs at the ends of the axis (when there are two legs on an end), and as well between the legs on the same sides of the axis.

The bridge member 14 has a top surface 20 and a bottom surface 22 which have corresponding shapes so that they are separated by a constant thickness for at least a portion, and preferably for at least 50%, and more preferably for at least 75% or even 90% of the surface area, and has a complex curving configuration. It extends along an axis preferably in a straight profile, but with a topography that can curve in either of two dimensions or optimally in both of two transverse directions. The shape includes two side edges 24, which may have an inwardly curving shape or may be represented by straight lines. The surfaces extending between the side edges 24 forming the top or outer surface and the bottom or inner surface of the bridge curve along the axis, in a shape that may define a portion of a circle, and they curve as well in a direction transverse to the axis. Both curves are convex relative to the bottom surface and can be the same or different radius curves. Preferably, the curves have the same inner radius dimensions so that the bridge member defines portions of spheres on the outer and inner surfaces and the radius is between 10-100 mm, and optimally is 50 mm+/−10 mm.

Figure 7:
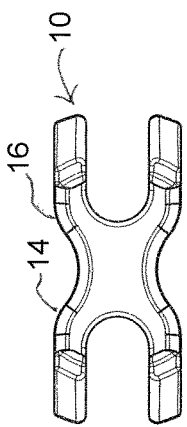
FIG. 7 shows a bottom view of the staple of FIG. 1.
Figure 1:
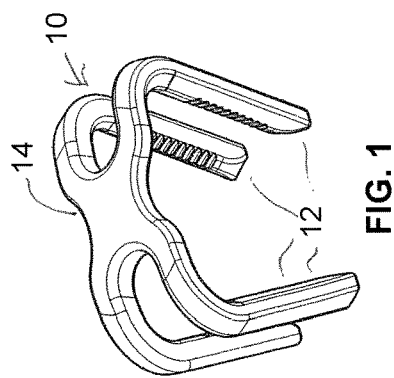
FIG. 1 shows a top perspective view of the staple in accordance with the present invention.
Figure 4:
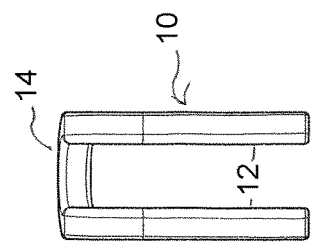
FIG. 4 shows a first end view of the staple of FIG. 1.
Figure 10:
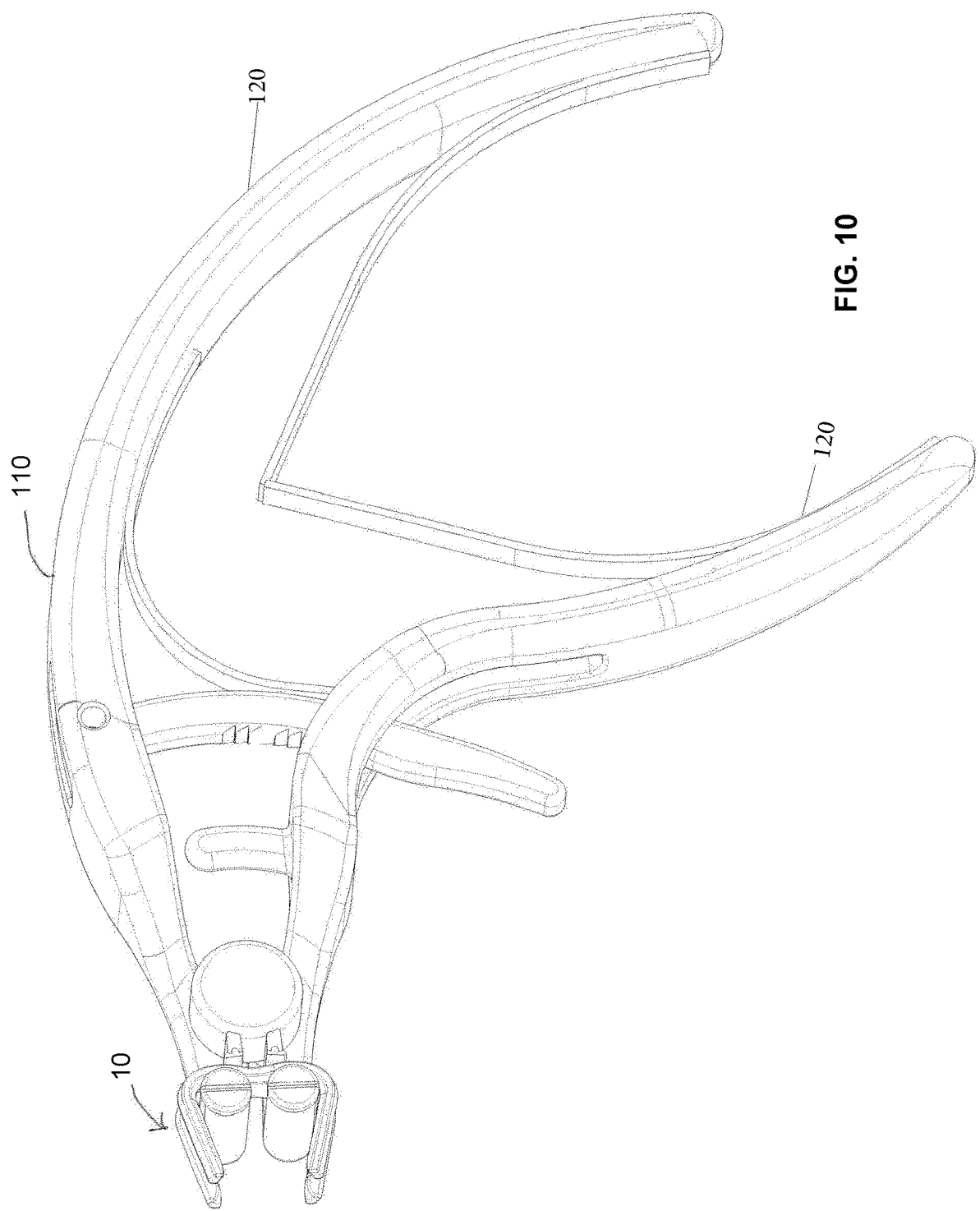
FIG. 10 shows side perspective of an inserter for the implantation of the staple of FIG. 1.
Figure 14:
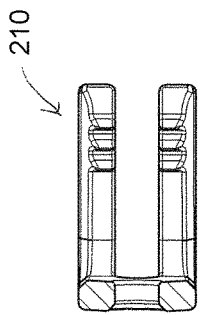
FIG. 14 is a cross section through line D-D as shown in FIG. 13.

The legs also optimally have an unusual and complex shape. While this can be a rectangle, they can form other polygons in cross section, and preferably pentagons. The legs may also include features 30 to help hold the legs in the bone, such as texturing, or ridges or barbs that help to hold the legs in position. Preferably, the surfaces of the legs that include this feature are opposing surfaces, such as surfaces that face an opposing leg as shown in the detail of FIG. 7. These ridges may include a series of spaced parallel ridges or alternating areas which in cross-section extend away from the base surface of the leg and return the base surface of the leg. Alternatively, the legs may include a series of grooves cut into the surface, or the legs may have a surface treatment, such as knurling, or cross-hatching. If they have ridges, the ridges may cover a portion of the vertical surface, such as 10-90%, and preferably from 25-50%. The ridges are lower profile than barbs, (for example only 0.25-2, and preferably 1+/−0.25 mm in height from the surface of the leg in order to permit earlier staple re-orientation and increased bone growth after removal.

Of a pair of opposing legs, either one or two legs may include these features. The legs have a cross-sectional configuration that provides for improved resistance to breaking as well as increased compressive forces, such as a polygonal shape that is not square. One preferred configuration is a rectangle or a five-sided figure illustrated in detail in FIG. 17 in which one corner of the rectangle, and preferably, an inside corner, is truncated to form the fifth side, and preferably, the five-sided shape having an aspect ratio greater than 2:1 of the larger sides to the smaller side in order to inherently increase the surface area of the legs and increase the compressive force of the staple. The staple may have two opposing legs, spaced apart from each other along the axis of the bridge member, or on one side it may have two legs, and one on the other, or it may have four legs which are situated to form a rectangle which circumscribes the bridge member. The staple is provided having a range of different bridge widths ranging from 10 mm to 25 mm and various leg lengths in the same range of length, so as to accommodate different fixation procedures in the forefoot, midfoot, rearfoot and hand.

Preferably, the staple is fabricated by machining a Nitinol blank to form a staple in the closed (converging legs) shape and the resulting staple is mechanically deformed during use to "load" the staple, meaning to induce the superelastic shape memory properties to compress bone segments and facilitate osteosynthesis. In this state, the staple has legs extending at a substantially transverse direction to the axis of the bridge in order to allow the staple to be inserted into pre-drilled pilot holes in the bone. Optimally, the staple is supplied pre-assembled but not pre-loaded on an inserter 110 or introducer in a sterile procedure pack containing disposable instrumentation. In this instance, the inserter 110 has a pair of pivoting handles 120 that are squeezed together to expand a pair of arm member bearing cylindrical holders that bias the staple legs open when the handles are engaged together.

Figure 17:
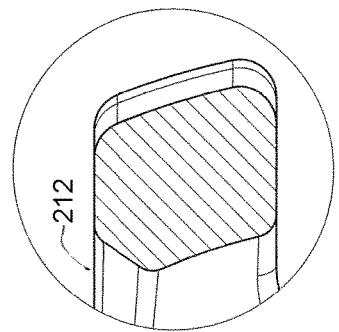
FIG. 17 is a detail of the top left leg in cross-section from FIG. 16.
Figure 13:
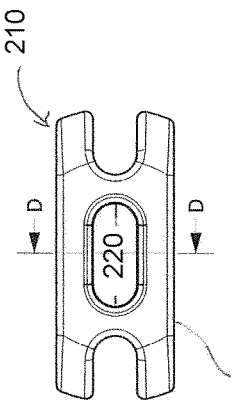
FIG. 13 is a top view of the staple of FIG. 12.
Figure 12:
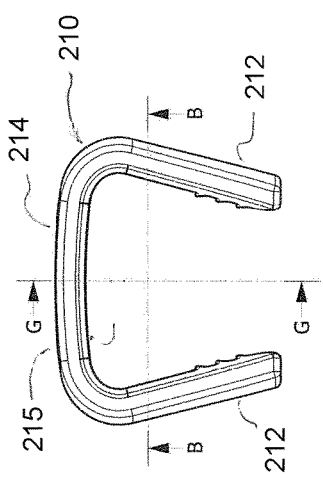
FIG. 12 is a side view of a second embodiment of the staple of the present invention.
Figure 16:
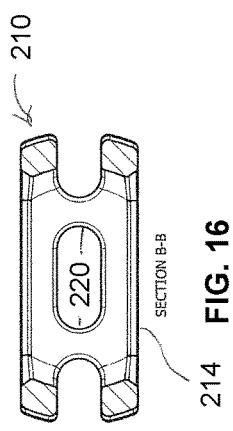
FIG. 16 is a cross-section through line B-B as shown in FIG. 12.
Figure 15:
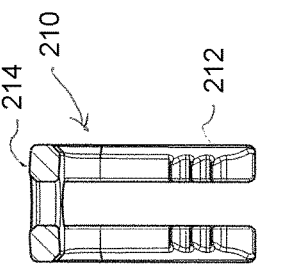
FIG. 15 is a cross-section through line G-G as shown in FIG. 12.

A further embodiment of the staple of the invention is shown in FIGS. 12 through 17. In these views, the staple is shown at 210, and comprises a generally u-shaped staple having a bridge member 214 that connects four legs 212 which extend away from the direction of the top and bottom surfaces 215 of the bridge member. These surfaces have shapes that mirror each other and a constant through thickness except where there is a middle fenestration or window 220 which allows for the insertion of bone implant material or to view the bone interface below the bridge of the staple. FIG. 17 illustrates the five-sided leg shape which is a four-sided trapezoid with a truncated corner to form the fifth side of the shape.

What is claimed is:

1. A staple, comprising:
    a superelastic material and having a bridge member having a top surface which includes a top surface area and an opposing bottom surface defining a constant thickness between for at least 90% of the top surface area, and the bridge member having an axis along a length between a first end and a second end and a first curve which is a portion of a circle or an ellipse along the axis and
    at least one pair of legs where the legs are straight and have a polygonal configuration in cross-section with rounded edges and with a short side having a length n and a longer side having a length of at least 2n, the configuration having five sides, and the legs are spaced apart along the axis and are joined to the bridge member by corner extensions which extend directly from the bridge member such that the bridge member top surface flows into a surface of each of the legs to allow the opposing bottom surface of the bridge member to sit flush in a bone.

2. A staple as set forth in claim 1, wherein the bridge member has a second curve transverse to the axis which is a portion of a circle or an ellipse.

3. A staple as set forth in claim 2, wherein said first curve is a portion of a circle and the second curve is a portion of a circle, the portions having different diameters.

4. A staple as set forth in claim 2, wherein said first curve is a portion of a circle and the second curve is a portion of a circle, the portions having the same diameters.

5. A staple as set forth in claim 1, wherein the staple has between two and six legs.

6. A staple as set forth in claim 1, wherein the staple has four legs placed at corners of a rectangle and the bridge includes a recess between the extension and the legs flow through the extensions into the bridge from an inwardly curved recess in the ends of the bridge member.

7. A staple as set forth in claim 1, wherein the superelastic material is Nitinol.

8. A staple as set forth in claim 1, wherein the bridge member further includes a fenestration.

9. A staple as set forth in claim 1 further comprising a first pair of a first straight leg and a second straight leg joined to the bridge member by a first corner extension and a second corner extension which flow smoothly into the first leg and the second leg from an inwardly curved recess in the first end of the bridge member along the axis, and a second pair of a first straight leg and a second straight leg joined by a first corner extension and a second extensions which flow smoothly into the first leg and the second leg from an inwardly curved recess in the second end of the bridge member and wherein each of the first and second leg of the first pair of legs and of the second pair of legs include an edge surface joined in a smooth uninterrupted contiguous surface through a surface of a corner extension with the top surface of the bridge member.

10. A staple as set forth in claim 9, wherein two of the pair of first legs and the second legs have a surface which includes an engagement feature.

11. A staple as set forth in claim 10, wherein the engagement feature is a plurality of ridges.

12. A staple as set forth in claim 9, wherein the polygonal configuration is a pentagon.

* * * * *